(12) United States Patent
Jonczyk et al.

(10) Patent No.: US 7,759,302 B2
(45) Date of Patent: Jul. 20, 2010

(54) PEPTIDIC SULFONAMIDES

(75) Inventors: Alfred Jonczyk, Darmstadt (DE); Ulrich Groth, Constance (DE); Gunther Zischinsky, Berlin (DE)

(73) Assignee: Merck Patent GmbH, Darmstadt (DE)

( * ) Notice: Subject to any disclaimer, the term of this patent is extended or adjusted under 35 U.S.C. 154(b) by 485 days.

(21) Appl. No.: 10/544,625

(22) PCT Filed: Jan. 14, 2004

(86) PCT No.: PCT/EP2004/000211

§ 371 (c)(1),
(2), (4) Date: Aug. 5, 2005

(87) PCT Pub. No.: WO2004/069861

PCT Pub. Date: Aug. 19, 2004

(65) Prior Publication Data

US 2006/0148716 A1 Jul. 6, 2006

(30) Foreign Application Priority Data

Feb. 6, 2003 (EP) .................................. 03002556

(51) Int. Cl.
*A61K 38/08* (2006.01)
(52) U.S. Cl. .............................. 514/2; 514/16; 530/329
(58) Field of Classification Search ........................ None
See application file for complete search history.

(56) References Cited

U.S. PATENT DOCUMENTS 6,245,809 B1 * 6/2001 Scarborough et al. ....... 514/534
6,660,843 B1 * 12/2003 Feige et al. .............. 530/391.7

FOREIGN PATENT DOCUMENTS

DE 199 29 410 12/2000

WO WO 00/37487 6/2000

OTHER PUBLICATIONS

The Journal of Biological Chemistry, Bd. 277, Nr. 37, Sep. 13, 2002, Seiten 33564-33570.

* cited by examiner

*Primary Examiner*—Christopher R. Tate
*Assistant Examiner*—Roy Teller
(74) *Attorney, Agent, or Firm*—Millen, White, Zelano, Branigan, P.C.

(57) ABSTRACT

The invention relates to novel peptides which are biologically active as ligands of blood platelet integrin GPIIbIIIa and the $\alpha_v$ integrins, preferably the $\alpha v\beta_5$ and $\alpha_v\beta_3$ integrin, having the formula (I): $R^1$-Arg-X-Asp-Leu-Asp-Ser-Leu-Arg-$R^2$ (I), in which $R^1$ denotes H, acetyl or acyl and $R^2$ denotes -Oh, $OR^3NH_2$, $NHR^3$, $N(R^3)_2$ $R^3$ denotes atkyl, aralkyl, aryl, Het and X denotes an amino acid of the formula (II), in which A denotes $(CH_2)_n$, $R^4$ denotes H, alkyl, aralkyl or aryl, and n denotes 1, 2, 3, 4, 5 or 6, and the amino acid of the formula (II) is bonded to the adjacent Arg via a peptide bond of the α-amino group and to the α-amino group of the adjacent Asp via a peptide bond of the α-carboxyl group.

$R^1$-Arg-X-Asp-Leu-Asp-Ser-Leu-Arg-$R^2$ (I)

(II)

9 Claims, No Drawings

SEQUENCE LISTING

```
<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Amino acid of the formula II
<220> FEATURE:
<223> OTHER INFORMATION: See specification as filed for detailed
      description of substitutions and preferred embodiments

<400> SEQUENCE: 1

Arg Xaa Asp Leu Asp Ser Leu Arg
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(Psa)

<400> SEQUENCE: 2

Arg Xaa Asp Leu Asp Ser Leu Arg
```

```
                            1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(F5-PSA)

<400> SEQUENCE: 3

Arg Xaa Asp Leu Asp Ser Leu Arg
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(2-NO2-PSA)

<400> SEQUENCE: 4

Arg Xaa Asp Leu Asp Ser Leu Arg
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(4-NO2-PSA)

<400> SEQUENCE: 5

Arg Xaa Asp Leu Asp Ser Leu Arg
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(2,4-NO2-PSA)

<400> SEQUENCE: 6

Arg Xaa Asp Leu Asp Ser Leu Arg
 1               5

<210> SEQ ID NO 7
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(6-OMe-PSA)

<400> SEQUENCE: 7

Arg Xaa Asp Leu Asp Ser Leu Arg
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(2-CF3-PSA)

<400> SEQUENCE: 8

Arg Xaa Asp Leu Asp Ser Leu Arg
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(3-CF3-PSA)

<400> SEQUENCE: 9

Arg Xaa Asp Leu Asp Ser Leu Arg
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(Me5-PSA)

<400> SEQUENCE: 10

Arg Xaa Asp Leu Asp Ser Leu Arg
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(4-tBu-PSA)
```

```
<400> SEQUENCE: 11

Arg Xaa Asp Leu Asp Ser Leu Arg
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(BSA)

<400> SEQUENCE: 12

Arg Xaa Asp Leu Asp Ser Leu Arg
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(iPrs)

<400> SEQUENCE: 13

Arg Xaa Asp Leu Asp Ser Leu Arg
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(1-Nap)

<400> SEQUENCE: 14

Arg Xaa Asp Leu Asp Ser Leu Arg
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(2-Nap)

<400> SEQUENCE: 15

Arg Xaa Asp Leu Asp Ser Leu Arg
 1               5
```

```
<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap(4-Ph-Psa)

<400> SEQUENCE: 16

Arg Xaa Asp Leu Asp Ser Leu Arg
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dap

<400> SEQUENCE: 17

Arg Xaa Asp Leu Asp Ser Leu Arg
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg(Pbf)
<220> FEATURE:
<221> NAME/KEY: MOD_RES
<222> LOCATION: (2)
<223> OTHER INFORMATION: Dap(Boc)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (5)
<223> OTHER INFORMATION: Asp(OBut)
<220> FEATURE:
<221> NAME/KEY: MOD_RES
<222> LOCATION: (6)
<223> OTHER INFORMATION: Ser(But)
<220> FEATURE:
<221> NAME/KEY: MOD_RES
<222> LOCATION: (8)
<223> OTHER INFORMATION: Arg(Pbf)

<400> SEQUENCE: 18

Arg Xaa Asp Leu Asp Ser Leu Arg
 1               5

<210> SEQ ID NO 19
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asp(OBut)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: Ser(But)
<220> FEATURE:
<221> NAME/KEY: MOD_RES
<222> LOCATION: (6)
<223> OTHER INFORMATION: Arg(Pbf)

<400> SEQUENCE: 19

Asp Leu Asp Ser Leu Arg
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg(Pbf)
<220> FEATURE:
<221> NAME/KEY: MOD_RES
<222> LOCATION: (2)
<223> OTHER INFORMATION: Dap
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (5)
<223> OTHER INFORMATION: Asp(OBut)
<220> FEATURE:
<221> NAME/KEY: MOD_RES
<222> LOCATION: (6)
<223> OTHER INFORMATION: Ser(But)
<220> FEATURE:
<221> NAME/KEY: MOD_RES
<222> LOCATION: (8)
<223> OTHER INFORMATION: Arg(Pbf)

<400> SEQUENCE: 20

Arg Xaa Asp Leu Asp Ser Leu Arg
  1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid

<400> SEQUENCE: 21

Arg Xaa Asp Leu Asp Ser Leu Arg
  1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Thr Asp Leu Asp Ser Leu Arg
 1               5
```

PEPTIDIC SULFONAMIDES

The invention relates to novel peptides, of the formula I

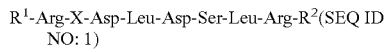

in which $R^1$ denotes H, acetyl or acyl and $R^2$ denotes —OH, $OR^3NH_2$, $NHR^3$, $N(R^3)_2$ $R^3$ denotes alkyl, aralkyl, aryl, Het and X denotes an amino acid of the formula II

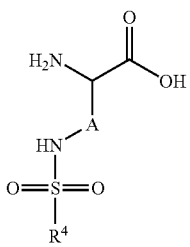

in which

A denotes $(CH_2)_n$ $R^4$ denotes H, alkyl, aralkyl or aryl, and n denotes 1, 2, 3, 4, 5 or 6, and the amino acid of the formula II is bonded to the adjacent Arg via a peptide bond of the α-amino group and to the α-amino group of the adjacent Asp via a peptide bond of the α-carboxyl group.

The present invention also relates to the pharmaceutically usable pro-drugs, derivatives, solvates and stereoisomers of the compounds of the formula I and the salts thereof, including mixtures thereof in all ratios.

The invention had the object of finding novel compounds having valuable properties, in particular those which can be used for the preparation of medicaments.

It has been found that the compounds of the formula I according to the invention and salts thereof have very valuable pharmacological properties while being well tolerated.

The compounds of the formula I according to the invention are ligands of blood platelet integrin GPIIbIIIa and the $\alpha_v$ integrins, preferably the $\alpha_v\beta_6$ and $\alpha_v\beta_3$ integrin, and are thus used as agonists and/or antagonists for the treatment of various diseases and pathological findings. They are furthermore used as diagnostic agents or reagents.

Other inhibitors of integrin $\alpha_v\beta_6$ are described in DE 19858857 and by S. Kraft et al. in J. Biol. Chem. 274, 1979-85 (1999).

Integrins belong to the family of heterodimeric class I transmembrane receptors, which play an important role in numerous cell-matrix and cell-cell adhesion processes (Tuckwell et al., 1996, Symp. Soc. Exp. Biol. 47). They can be divided roughly into three classes: the $\beta_1$ integrins, which are receptors for the extracellular matrix, the $\beta_2$ integrins, which can be activated on leucocytes and are triggered during inflammatory processes, and the $\alpha_v$ integrins, which influence the cell response in wound-healing and other pathological processes (Marshall and Hart, 1996, Semin. Cancer Biol. 7, 191).

The $\alpha_5\beta_1$, $\alpha_{IIb}\beta_3$, $\alpha_8\beta_1$, $\alpha_v\beta_1$, $\alpha_v\beta_3$, $\alpha_v\beta_5$, $\alpha_v\beta_8$ and $\alpha_v\beta_6$ integrins all bind to the Arg-Gly-Asp (RGD) peptide sequence in natural ligands, such as, for example, fibronectin or vitronectin. Soluble RGD-containing peptides are capable of inhibiting the interaction of each of these integrins with the corresponding natural ligands.

$\alpha_v\beta_6$ is a relatively rare integrin (Busk et al., 1992 J. Biol. Chem. 267(9), 5790; Breuss et al., 1993, J. Histochem. Cytochem. 41(10), 1521), which is increasingly formed in repair processes in epithelial tissue and preferentially binds the natural matrix molecules fibronectin and tenascin (Wang et al., 1996, Am. J. Respir. Cell Mol. Biol. 15(5), 664; Huang et al., 1998, J. Cell Sci. 111, 2189). The physiological and pathological functions of $\alpha_v\beta_6$ are not yet known precisely, but it is assumed that this integrin plays an important role in physiological processes and diseases (for example inflammation, wound healing, tumours) in which epithelial cells are involved (Breuss et al., 1995, J. Cell Sci. 108, 2241). Thus, $\alpha_v\beta_6$ is expressed on keratinocytes in wounds (Haapasalmi et al., 1996, J. Invest. Dermatol. 106 (1), 42; Cass et al., 1998, J. Pediatr. Surg. 33 (2), 312), from which it can be assumed that, besides wound-healing processes and inflammation, other pathological events on the skin, such as, for example, psoriasis, can also be influenced by agonists or antagonists of the said integrin.

Furthermore, hornification disorders of the skin, so-called leukoplakia, in the mucosa of the oral cavity, on the lips, the tongue, and the genitals exhibit increased expression of integrin $\alpha_v\beta_6$, in contrast to normal comparative tissue. It has also been found that the frequency and level of expression of the leukoplakia increases, via lichen planus, to squamous cell carcinoma, i.e. that the expression of $\alpha_v\beta_6$ may be associated with the malignant transformation of leukoplakia (Hamidi et al., 2000, Br. J. Cancer. 82 (8), 1433; Ramos et al., 1997, Int. J. Cancer. 72 (2), 369; Thomas et al., 2001, J. Inv. Dermatol. 117 (1), 67; Koivisto et al., 2000, Exp. Cell Res. 255 (1), 10).

Furthermore, $\alpha_v\beta_6$ plays a role in the respiratory tract epithelium (Weinacker et al., 1995, Am. J. Respir. Cell Mol. Biol. 12 (5), 547), meaning that corresponding agonists/antagonists of this integrin could successfully be employed in respiratory tract diseases, such as bronchitis, asthma, lung fibroses and respiratory tract tumours (Huang et al., 1998, Am. J. Respir. Cell Mol. Biol. 19 (4), 636; Pilewski et al., 1997, Am. J. Physiol. 273, L256; Kaminski et al., 2000, Proc. Natl. Acad. Sci. USA. 97 (4), 1778).

Fibroses are not only known in the lung (bronchia), they are also found in other organs, meaning that integrin $\alpha_v\beta_6$ also plays a role therein; examples are pathological connecting tissue proliferation, for example of the skin, the liver (as far as cirrhosis), the kidney and the bladder, the heart and the pancreas (cystic fibrosis) (Mutsaers et al., 1997, J. Int. J. Biochem. Cell Biol. 29 (1), 5; Dalton, S. L. 1999, J. Am. Acad. Dermatol. 41, 457; Kropf et al., 1991, Z. Med. Laboratoriumsdiagn. 32 (3/4), 150; Schnee et al., 2000, Cardiovasc. Res. 46 (2), 264; Sime, P. J. 1999 Curr. Opin. Anti-Inflammatory Immunomodulatory Invest. Drugs 1 (5), 423; Housset et al., 1999, J. Pathol. Biol. 47 (9), 886; Norman et al., 1999, Exp. Nephrol. 7 (2), 167; Nahas et al., 1997, Int. J. Biochem. Cell Biol. 29 (1), 55). It is likewise known that $\alpha_v\beta_6$ also plays a role in the intestinal epithelium, meaning that corresponding integrin agonists/antagonists could be used in the treatment of inflammation, tumours and wounds of the stomach/intestinal tract. There are indications here that integrin $\alpha_v\beta_6$ also influences the secretion of matrix metalloproteases, such as, for example, that of gelatinase B (MMP-9) (Agrez et al., 1994, J. Cell. Biol. 127 (2), 547; Niu et al., 1998, Biochem. Biophys. Res. Commun. 249 (1), 287).

The regulation of MMP activity (possibly of different MMPs) by tumour cells as a function of their density is also a mechanism which enables the cells to create further space for proliferation and migration by proteolysis of the surrounding matrix during growth of the tumour mass. This connection between $\alpha_v\beta_6$ expression, cell density and MMP activity is referred to in the literature (Niu et al., 2001, Int. J. Cancer 92 (1), 40; Agrez et al., 1999 Int. J. Cancer 81 (1), 90; Thomas et al., 2001, J. Inv. Dermatol. 116 (6), 898; Thomas et al., 2001 Int. J. Cancer 92 (5), 641).

Since integrin $\alpha_v\beta_6$ is involved in infection processes, its agonists/antagonists can be used in microbial infections (protozoa, microphytes; bacteria, viruses, yeasts, fungi). Examples are known for the coxsackievirus and for the infection of host cells with the foot-and-mouth disease virus (FMDV), which proceed $\alpha_v\beta_3$-dependently, but can also take place $\alpha_v\beta_6$ dependently (Agrez et al., 1997, Virology. 239 (1), 71; Jackson et al., 2000, J. Virol. 74 (11), 4949; Miller et al., 2001, J. Virol. 75 (9), 4158; Neff et al., 2001, J. Virol. 75 (1), 527; Neff et al., 1998, J. Virol. 72 (5), 3587; Jackson et al., 1997 J. Virol. 71 (11), 8357).

Infection with HIV (AIDS) is also dependent on $\alpha_v$ integrins, as has already been shown years ago (Ruoslahti et al., WO 92/14755).

According to more recent knowledge, the bacterium *Bacillus anthracis* secretes a toxin that consists of 3 proteins, one of which, the so-called PA or protective antigen, binds to receptors on the cell membrane, and the ATR (anthrax toxin receptor) receptor described here is a type I membrane protein with an extracellular domain of the von Willebrandt factor A type. Integrins also contain such vWFA domains. This is comprehensible both for integrin $\alpha_v\beta_6$ by homology analysis in the Swiss Prot database (http://www.expasy.ch/cgi-bin/niceprot.pl?P18564; here sequence $\beta_6$ (131-371)), and also for $\alpha_v\beta_3$ (http://www.expasy.ch/cgi-bin/niceprot.pl?P05106; $\beta_3$ (135-377)). The agonists/antagonists according to the invention can therefore also be used in the case of anthrax of the lung, skin and intestine (Bradley et al., 2001, Nature 414, 225; Tuckwell, 1999, Biochem. Soc. Trans. 27 (6), 835).

The dependence of the infection of host cells on their adhesion receptors has also been described for bacteria, and for yeasts (budding fungi, *candida*) (Kerr, J R. 1999 Medical Microbiology, Manchester Royal Infirmary, UK, MOLECULAR PATHOLOGY, 52 (4), 220; Dehio et al., 1998, FEBS LETT. 424 (1-2), 84; Stockbauer et al., 1999 Proc. Nat. Acad. Sci. USA. 96 (1), 242; Santoni et al., 2001 Microbial Pathogen. 31 (4), 159).

The interaction of integrin $\alpha_v\beta_6$ with TGF-$\beta$ and the activation resulting from this has been demonstrated. (Dalton, S L. 1999, J. Am. Acad. Dermatol 41, 457; Munger et al., 1999 Cell 96, 319).

It has been published that latent TGF$\beta$1 (i.e. one of the pro-forms) binds to integrin $\alpha_v\beta_6$ and is then activated proteolytically. The compounds according to the invention could inhibit the binding of TGF-$\beta$ (pro-form, LAP peptide, LAP-TGF$\beta$, latent TGF) to the integrin, and agonists/antagonists of integrin $\alpha_v\beta_6$ could thereby prevent activation of TGF-$\beta$1 and other subtypes. Modulation of TGF$\beta$ would thereby be facilitated.

To date, 3 human TGF$\beta$ isoforms have been discovered to which is ascribed a role in a multiplicity of growth and differentiation processes, but in particular in inflammatory processes, fibroses, wound healing, bone growth, modulation of immune functions, in angiogenesis and tumour metastasis (Rifkin et al., 1993, 70, 177; Hata et al., 1998, Mol. Med. Today 257; Sheppard, D. 2001, Chest. 120 (1 Suppl), 49S; Wickstom et al. 1998, Prostate 37, 19). It can be assumed that it will also be possible to use the compounds according to the invention as agonists/antagonists of $\alpha_v\beta_6$ in these processes.

A further paper which emphasises the role of $\alpha_v\beta_6$ in immunological processes describes the influx of neutrophiles after chemical damage of the lung (Miller et al., 2001, J. Histochem. Cytochem. 49 (1), 41).

The dependence of the occurrence of angiogenesis on the interaction between vascular integrins and extracellular matrix proteins is described by P. C. Brooks, R. A. Clark and D. A. Cheresh in Science 264, 569 (1994).

The object was thus, besides the natural high-molecular-weight ligands and antibodies known to date, which are difficult to handle therapeutically and diagnostically, to find potent, specific and/or selective low-molecular-weight peptidic ligands for blood platelet integrin GPIIbIIIa and for the $\alpha_v$ integrins, preferably for $\alpha_v\beta_6$ and $\alpha_v\beta_3$, which can be used in the said therapeutic areas, but also as diagnostic agent or reagent.

It has been found that the peptidic compounds according to the invention and salts thereof exert an action on blood platelet integrin GPIIbIIIa and the $\alpha_v$ integrins, preferably on $\alpha_v\beta_6$ and $\alpha_v\beta_3$ integrins, or cells carrying these integrins, or, if they are bound to surfaces, represent synthetic ligands for the binding of isolated GPIIbIIIa or of isolated $\alpha_v$ integrins, preferably $\alpha_v\beta_6$ and $\alpha_v\beta_3$ integrins or GPIIbIIIa- or $\alpha_v$-promoted functions of the cells. In particular, they act as GPIIbIIIa integrin, $\alpha_v$ integrin, preferably $\alpha_v\beta_6$ and/or $\alpha_v\beta_3$ integrin inhibitors, inhibiting, in particular, the interactions of the receptor with other ligands, such as, for example, the binding of fibronectin. This action can be detected, for example, by the method described by Smith et al. in J. Biol. Chem. 265, 12267-12271 (1990).

It has furthermore been found that the novel substances have very valuable pharmacological properties while being well tolerated and can be employed as medicaments. This is described in greater detail below.

These properties are retained even if the amino acids which are not in position X are replaced, and/or the linear compounds are cyclised, as described in WO 01/00660 and WO 01/05810.

The peptidic compounds according to the invention can furthermore be used as diagnostic agents for the detection and localisation of pathological states in epithelial system in vivo if they are provided with corresponding marker molecules in accordance with the prior art. Suitable for this purpose is, for example, biotin (for example for affinity purposes), or various fluorescent labels or radioisotope complexes for diagnosis and imaging methods. The compounds according to the invention may also carry anchor functions in order to be coupled covalently to surfaces of workpieces, such as, for example, bio implants, microtitre plates or particles.

The invention also encompasses combinations with at least one other active ingredient and/or conjugates with other active ingredients, such as cytotoxic active ingredients and conjugates with radiomarkers for X-ray therapy or PET diagnosis, but also fusion proteins with marker proteins, such as GFP or antibodies, or therapeutic proteins, such as IL-2.

For the purposes of the present invention, alkyl denotes a linear or branched or cyclic alkyl radical having 1, 2, 3, 4, 5, 6, 7, 8, 9, 10, 11, 12, 13, 14, 15, 16, 17 or 18 C atoms, which may be substituted, for example halogenated, hydroxylated, animated, partially unsaturated or interrupted by hetero atoms, such as N, S or O. If an alkyl radical is substituted by halogen, it preferably has, depending on the number of carbon atoms of the alkyl radical, 1, 2, 3, 4 or 5 halogen atoms. Thus, for example, a methyl group can be mono-, di- or trisubstituted by halogen, and an ethyl group can be mono-, di-, tri-, tetra- or pentasubstituted by halogen. Alkyl preferably stands for methyl, ethyl, trifluoromethyl, pentafluoroethyl or propyl, particularly preferably for isopropyl, butyl, isobutyl, sec-butyl or tert-butyl, but also for n-pentyl, neopentyl or isopentyl.

The term "aryl" encompasses an unsubstituted or mono- or polysubstituted aromatic mono-, bi- or tricyclic hydrocarbon radical, such as, for example, a benzene ring or anthracene, phenanthrene or naphthalene ring systems. Examples of suitable substituents encompass $NO_2-$, $F-$, $Cl-$, $Br-$, $I-$, $HO-$, $H_2N-$, $R^3HN-$, $(R^3)_2N-$, alkyl-, alkyl-O-, $CF_3-O-$, alkyl-CO-, aryl-, aryl-O-, aryl-CO-, aryl-CONH-, arylSO$_2-$, arylSO$_2-$HN-, where the substituents may occur, independently of one another, 0 to 5 times.

The term "Het" encompasses an unsubstituted or mono- or polysubstituted, saturated, unsaturated or aromatic mono-, bi- or tricyclic heterocyclic radical. As hetero atoms, S, N or O may occur one to three times. Examples of suitable substituents encompass $NO_2-$, $F-$, $Cl-$, $Br-$, $I-$, $HO-$, $H_2N-$, $R^3HN-$, $(R^3)_2N-$, alkyl-, alkyl-O-, $CF_3-O-$, alkyl-CO-, aryl-, aryl-O-, aryl-CO-, aryl-CONH-, arylSO$_2-$, arylSO$_2-$HN-, where the substituents may occur, independently of one another, 0 to 5 times.

The term "aralkyl" preferably encompasses an aryl radical as defined above bonded to an alkyl radical as defined above. Examples of suitable aralkyl radicals encompass, but are not restricted to, benzyl, phenylpropyl, phenylbutyl and the like.

The term $α_v$ integrins in the present invention encompasses integrins $α_vβ_1$, $α_vβ_3$, $α_vβ_5$, $α_vβ_6$ and $α_vβ_8$, but preferably the $α_vβ_6$ and $α_vβ_3$ integrin.

The invention relates, in particular, to peptidic compounds selected from the group of the formulae I a)-I o)

| Ac-Arg-Dap(Psa)-Asp-Leu-Asp-Ser-Leu-Arg-NH$_2$ (SEQ ID NO: 2), | I a) |
| Ac-Arg-Dap(F5-PSA)-Asp-Leu-Asp-Ser-Leu-Arg-NH$_2$(SEQ ID NO: 3), | I b) |
| Ac-Arg-Dap(2-NO$_2$-PSA)-Asp-Leu-Asp-Ser-Leu-Arg-NH$_2$(SEQ ID NO: 4), | I c) |
| Ac-Arg-Dap(4-NO$_2$-PSA)-Asp-Leu-Asp-Ser-Leu-Arg-NH$_2$(SEQ ID NO: 5), | I d) |
| Ac-Arg-Dap(2,4-NO$_2$-PSA)-Asp-Leu-Asp-Ser-Leu-Arg-NH$_2$(SEQ ID NO: 6), | I e) |
| Ac-Arg-Dap(6-OMe-PSA)-Asp-Leu-Asp-Ser-Leu-Arg-NH$_2$(SEQ ID NO: 7), | I f) |
| Ac-Arg-Dap(2-CF$_3$-PSA)-Asp-Leu-Asp-Ser-Leu-Arg-NH$_2$(SEQ ID NO: 8), | I g) |
| Ac-Arg-Dap(3-CF$_3$-PSA)-Asp-Leu-Asp-Ser-Leu-Arg-NH$_2$(SEQ ID NO: 9), | I h) |
| Ac-Arg-Dap(Me$_5$-PSA)-Asp-Leu-Asp-Ser-Leu-Arg-NH$_2$(SEQ ID NO: 10), | I i) |
| Ac-Arg-Dap(4-tBu-PSA)-Asp-Leu-Asp-Ser-Leu-Arg-NH$_2$(SEQ ID NO: 11), | I j) |
| Ac-Arg-Dap(BSA)-Asp-Leu-Asp-Ser-Leu-Arg-NH$_2$ (SEQ ID NO: 12), | I k) |
| Ac-Arg-Dap(iPrs)-Asp-Leu-Asp-Ser-Leu-Arg-NH$_2$ (SEQ ID NO: 13), | I l) |
| Ac-Arg-Dap(1-Nap)-Asp-Leu-Asp-Ser-Leu-Arg-NH$_2$ (SEQ ID NO: 14), | I m) |
| Ac-Arg-Dap(2-Nap)-Asp-Leu-Asp-Ser-Leu-Arg-NH$_2$ (SEQ ID NO: 15), | I n) |
| Ac-Arg-Dap(4-Ph-Psa)-Asp-Leu-Asp-Ser-Leu-Arg-NH$_2$(SEQ ID NO: 16), | I o) | and pharmaceutically usable prodrugs, derivatives, solvates and stereoisomers thereof, and salts thereof, including mixtures thereof in all ratios, where the abbreviations used in brackets in the formulae I a)-I o) stand for the following radicals:

| | |
|---|---|
| Psa | phenylsulfonyl radical |
| F5-PSA | pentafluorophenylsulfonyl radical |
| 2-NO$_2$-PSA | 2-nitrophenylsulfonyl radical |
| 4-NO$_2$-PSA | 4-nitrophenylsulfonyl radical |
| 2,4-NO$_2$-PSA | 2,4-dinitrophenylsulfonyl radical |
| 6-OMe-PSA | 6-methoxyphenylsulfonyl radical |
| 2-CF$_3$-PSA | 2-trifluoromethylphenylsulfonyl radical |
| 3-CF$_3$-PSA | 3-trifluoromethylphenylsulfonyl radical |
| Me$_5$-PSA | pentamethylphenylsulfonyl radical |
| 4-tBu-PSA | 4-tert-butylphenylsulfonyl radical |
| Bsa | benzylsulfonyl radical |
| iPrs | isopropylsulfonyl radical |
| 1-Nap | 1-naphthylsulfonyl radical |
| 2-Nap | 2-naphthylsulfonyl radical |
| 4-Ph-Psa | 4-phenylphenylsulfonyl radical |

The abbreviations mentioned above and below for amino acid radicals stand for the radicals of the following amino acids:

| | |
|---|---|
| Asp or D | aspartic acid |
| Arg or R | arginine |
| Dap | 2,3-diaminopropionic acid |
| Leu or L | leucine |
| Ser or S | serine |
| Thr or T | threonine |

Furthermore, the following abbreviations above and below have the following meanings:

| | |
|---|---|
| Ac | acetyl |
| BOC | tert-butoxycarbonyl |
| BSA | bovine serum albumin |
| CBZ or Z | benzyloxycarbonyl |
| DCCI | dicyclohexylcarbodiimide |
| DCM | dichloromethane |
| DIEA | diisopropylamine |
| DMA | N,N-dimethylacetamide |
| DMF | dimethylformamide |
| EDCI | N-ethyl-N,N'-(dimethylaminopropyl)carbodiimide |
| Et | ethyl |
| FCA | fluoresceincarboxylic acid |
| FITC | fluorescein isothiocyanate |
| Fmoc | 9-fluorenylmethoxycarbonyl |
| Fmoc-Dap(ivDde) | N-α-Fmoc-N-γ-1-(4,4-dimethyl-2,6-dioxocyclohex-1-yli-dene)-3-methylbutyldiaminopropionic acid |
| FTH | fluoresceinthiourea |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| NMP | N-methylpyrrolidone |
| HONSu | N-hydroxysuccinimide |
| OBut | tert-butyl ester |
| Oct | octanoyl |
| OMe | methyl ester |
| OEt | ethyl ester |

-continued

| | |
|---|---|
| Pbf | 2,2,4,6,7-pentamethyldihydrobenzofuran-5-sulfonyl |
| Pmc | 2,2,5,7,8-pentamethylchroman-6-sulfonyl |
| POA | phenoxyacetyl |
| Sal | salicyloyl |
| TBS++ | Tris buffered saline with divalent cations |
| TBSA | TBS + BSA |
| TBTU | 2-(1H-benzotriazol-1-yl)-1,1,3-tetramethyluronium tetrafluoroborate |
| TFA | trifluoroacetic acid |
| TIS | triisopropylamine |
| Trt | trityl(triphenylmethyl). |

If the above-mentioned amino acids can occur in a plurality of enantiomeric forms, all these forms and also mixtures thereof (for example the DL forms) are included above and below. Furthermore, the amino acids may be provided with corresponding protecting groups known per se.

The compounds according to the invention also include so-called prodrug derivatives, i.e. compounds which are modified with, for example, alkyl or acyl groups, sugars or oligopeptides and which are rapidly cleaved in the organism to give the effective compounds according to the invention. These also include biodegradable polymer derivatives of the compounds according to the invention, as described, for example, in Int. J. Pharm. 115, 61-67 (1995).

The said amino acids and amino acid radicals, such as, for example, the NH functions or also the C-terminal amide function, may also be derivatised, with the N-methyl, N-ethyl, N-propyl, N-benzyl or $C_\alpha$-methyl derivatives being preferred. Furthermore, derivatives of Asp, in particular those with methyl, ethyl, propyl, butyl, tert-butyl, neopentyl or benzyl esters of the side-chain carboxyl groups, furthermore also derivatives of Arg, which may be substituted by an acetyl, benzoyl, methoxycarbonyl or ethoxycarbonyl radical on the —NH—C(=NH)—NH$_2$ group, may occur.

Besides the compounds of the formula I which carry an acetyl group on the N terminal, the compounds according to the invention also include compounds in which Ac has been replaced by another acyl function, such as, for example, propionyl, butyryl or also benzoyl.

Furthermore, the compounds according to the invention also include derivatives which consist of the actual compounds according to the invention which have been derivatised with known marker molecules which enable the peptides to be detected easily. Examples of such derivatives are radioactively labelled, biotinylated or fluorescence-labelled peptides.

Fluorescent dye radical preferably denotes 7-acetoxycoumarin-3-yl, fluorescein-5-(and/or 6-)yl, 2',7'-dichlorofluorescein-5-(and 6-)yl, dihydrotetramethylrosamin-4-yl, tetramethylrhodamin-5-(and/or 6-)yl, 4,4-difluoro-5,7-dimethyl-4-bora-3a,4a-diaza-s-indacen-3-ethyl or 4,4-difluoro-5,7-diphenyl-4-bora-3a,4a-diaza-s-indacen-3-ethyl.

Suitable functionalised fluorescent dye radicals which can serve as reagents for the preparation of the compounds of the formula I according to the invention are, for example, described in "Handbook of Fluorescent Probes and Research Chemicals, 5th Edition, 1992-1994, by R. P. Haughland, Molecular Probes, Inc."

In general, the peptides according to the invention are linear, but they may also be cyclised. The invention encompasses not only the said peptides, but also mixtures and compositions which, besides these compounds according to the invention, also comprise other pharmacological active ingredients or adjuvants which can influence the primary pharmacological action of the peptides according to the invention in the desired manner.

The compounds according to the invention and also the starting materials for their preparation are, in addition, prepared by methods known per se and frequently employed, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants which are known per se.

The peptides according to the invention can preferably be prepared by solid-phase synthesis and subsequent cleavage and purification, as described, for example, by Jonczyk and Meienhofer (Peptides, Proc. 8th Am. Pept. Symp., Eds. V. Hruby and D. H. Rich, Pierce Comp. III, p. 73-77, 1983, or Angew. Chem. 104, 1992, 375) or by the method of Merrifield (J. Am. Chem. Soc. 94, 1972, 3102).

The peptides according to the invention can be prepared on the solid phase (manually or in an automatic synthesiser) in an Fmoc strategy with acid-labile side protecting groups and purified by means of RP-HPLC. The peak uniformity can be measured by RP-HPLC and the substance identity by means of FAB-MS.

In addition, the peptides can be prepared by conventional methods of amino-acid and peptide synthesis, as known, for example, from Novabio-chem—1999 Catalog & Peptide Synthesis Handbook of Calbiochem-Novabiochem GmbH, D-65796 Bad Soden, from numerous standard works and published patent applications.

Stepwise couplings and fragment condensations can also be used. Use can be made of various N-terminal, C-terminal and side protecting groups, which are preferably selected so as to be orthogonally removable. Coupling steps can be carried out with various condensation reagents, such as carbodiimides, carboduimidazole, those of the uronium type, such as TBTU, mixed anhydride methods, and acid halide or activated ester methods.

Cyclisation of a linear precursor molecule with side protecting groups can likewise be carried out with condensation reactions of this type, as described, for example, in DE 43 10 643 or in Houben-Weyl, I.c., Volume 15/II, pages 1 to 806 (1974).

Various resins and anchor functions can be used in the solid-phase peptide synthesis. Resins may be based, for example, on polystyrene or polyacrylamide, anchor functions, such as Wang, o-chlorotrityl, can be used for the preparation of peptide acids, aminoxanthenoxy anchors, for example for the preparation of peptide amides. (cf.; Principles of Peptide Synthesis, ed. M. Bodansky, Springer Verlag Berlin 1984; Houben Weyl Methoden der organischen Chemie [Methods of Organic Chemistry], Georg Thieme Verlag, Stuttgart; Calbiochem/Novabiochem Catalogue and Synthesis Handbook 1999, Synthesis Notes; Peptide Synthesis Protocols eds. M. W. Pennington and B. M. Dunn in Methods in Molecular Biology Vol 35, Humana Press Totowa N.J. 1994)

Biotinylated or fluorescence-labelled peptides/proteins can likewise be prepared by standard methods (for example E. A. Bayer and M. Wilchek in Methods of Biochemical Analysis Vol 26 The Use of the Avidin-Biotin Complex as a Tool in Molecular Biology; and Handbook of Fluorescent Probes and Research Chemicals, 6$^{th}$ Edition, 1996, by R. P. Haughland, Molecular Probes, Inc.; or also WO 97/14716).

The peptides according to the invention can of course also be liberated by solvolysis, in particular hydrolysis, or by hydrogenolysis of their functional derivatives. Preferred starting materials for the solvolysis or hydrogenolysis are those which, instead of one or more free amino and/or hydroxyl groups, contain corresponding protected amino and/or hydroxyl groups, preferably those which carry an amino-protecting group instead of an H atom bonded to an N atom or which carry a hydroxyl-protecting group instead of the H atom of a hydroxyl group. The corresponding situation applies to carboxylic acids, which can be protected by substitution of their —CO—OH hydroxyl function by means of a protecting group, for example as esters.

The term "amino-protecting group" is generally known and relates to groups which are suitable for protecting (blocking) an amino group against chemical reactions, but which are readily removable after the desired chemical reaction has been carried out elsewhere in the molecule. The term "hydroxyl-protecting group" is likewise generally known and relates to groups which are suitable for protecting a hydroxyl group against chemical reactions, but which are readily removable after the desired chemical reaction has been carried out elsewhere in the molecule. The liberation of the compounds from their functional derivatives is carried out—depending on the protecting group used—for example using strong acids, advantageously using TFA, HBr or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. Hydrogenolytically removable protecting groups (for example CBZ or benzyl) can be removed, for example, by treatment with hydrogen in the presence of a catalyst (for example a noble-metal catalyst, such as palladium, advantageously on a support, such as carbon).

Typical protecting groups for N termini and for pendant amino groups are Z, BOC, Fmoc, those for C termini or the Asp side chains are O-(prim. alkyl) (for example OMe or OEt), O-tert-alkyl (for example OBut) or O-benzyl. For the guanidino function of the Arg, Z, BOC, $NO_2$, Mtr, Pmc or Pbf, for example, is suitable. Alcoholic functions can be protected by tert-alkyl radicals, benzyl radical or trityl groups.

The groups BOC, OBut and Mtr can, for example, preferably be removed using TFA in dichloromethane or using approximately 3 to 5 n HCl in dioxane at 15-30°, the FMOC group using an approximately 5 to 50% solution of dimethylamine, diethylamine or piperidine in DMF at 15-30°.

Hydrogenolytically removable protecting groups (for example CBZ or benzyl) can be removed, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, ethers, such as THF or dioxane, or amides, such as DMF, DMA or NMP. The hydrogenolysis is generally carried out at temperatures between about 0 and 100° and pressures between about 1 and 200 bar, preferably at 20-30° and 1-10 bar. Hydrogenolysis of the CBZ group succeeds, for example, well on 5 to 10% Pd/C in methanol or using ammonium formate (instead of hydrogen) on Pd/C in methanol/DMF at 20-30°.

As already mentioned, the salts of the compounds of the formula I and the salts of the usable prodrugs, derivatives, solvates and stereoisomers of the compounds of the formula I are likewise encompassed. These can be prepared by standard methods. Thus, a base of a compound according to the invention can be converted into the associated acid-addition salt using an acid, for example by reaction of equivalent amounts of the base and the acid in an inert solvent, such as ethanol, and subsequent evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds according to the invention. On the other hand, an acid of the compounds according to the invention can be converted into one of its physiologically acceptable metal or ammonium salts by reaction with a base. Suitable salts here are, in particular, the sodium, potassium, magnesium, calcium and ammonium salts, furthermore substituted ammonium salts, for example the dimethyl-, diethyl- or diisopropylammonium salts, monoethanol-, diethanol- or diisopropylammonium salts, cyclohexyl-, dicyclohexylammonium salts, dibenzylethylenediammonium salts, furthermore, for example, salts with arginine or lysine.

The peptidic compounds according to the invention can, as already mentioned, be employed as medicament active ingredients in human and veterinary medicine for prophylaxis and/or therapy. Particular emphasis should be placed here on circulatory diseases, pulmonary embolism, thrombosis, in particular deep-vein thrombosis, cardiac infarction, arteriosclerosis, aneurysma dissecans, transient ischaemic attacks, apoplexy, angina pectoris, in particular unstable angina pectoris, pathological connecting tissue proliferation in organs or fibroses, in particular pulmonary fibrosis, but also cystic fibrosis, dermatofibrosis, hepatic fibroses, liver cirrhosis, urethrofibroses, renal fibrosis, cardiac fibrosis, infantile endocardial fibrosis, pancreatic fibrosis, hornification disorders of the skin, leukoplakia, lichen planus, and squamous cell carcinoma, tumour diseases, such as tumour development, tumour angiogenesis or tumour metastasis, of solid tumours and those of the blood or immune system, for example tumours of the skin, squamous cell carcinoma, tumours of the blood vessels, of the gastrointestinal tract, of the lung, of the breast, of the liver, of the kidney, of the spleen, of the pancreas, of the brain, of the testes, of the ovary, of the womb, of the vagina, of the muscles, of the bones, and those of the throat and head area, osteolytic diseases, such as osteoporosis, hyperparathyroidism, Paget's disease, malignant hypercalcaemia, incompatible blood transfusion, pathological angiogenic diseases, such as, for example, inflammation, ophthalmological diseases, diabetic retinopathy, macular degeneration, myopia, corneal transplant, rubeotic glaucoma, ocular histoplasmosis, rheumatic arthritis, osteoarthritis, ulcerative colitis, Crohn's disease, atherosclerosis, psoriasis, restenosis, in particular after angioplasty, multiple sclerosis, pregnancy, absumptio placentaris, viral, bacterial, yeast and fungal infections, foot-and-mouth disease, HIV, anthrax, *candida albicans*, in the case of acute kidney failure and in the case of wound healing for supporting the healing process.

The invention accordingly relates to peptidic compounds of the formulae defined above and below and in the claims, including physiologically acceptable salts thereof, as medicaments, diagnostic agents or reagents.

In particular, the invention relates to corresponding medicaments as inhibitors for combating the above-mentioned diseases in which GPIIbIIIa, $\alpha_v$ integrins, preferably $\alpha_v\beta_6$ and/or $\alpha_v\beta_3$ integrin, are involved, thus, in particular, in circulatory diseases, pathological connecting tissue proliferation in organs and fibroses, hornification disorders, tumour diseases, osteolytic diseases, pathologically angiogenic diseases, infections and for influencing wound-healing processes.

The invention also relates to corresponding pharmaceutical compositions which comprise at least one compound of the formula I or a physiologically acceptable prodrug, derivative, solvate or stereoisomer or a salt thereof and optionally excipients and/or adjuvants.

The invention also relates to a set (kit) consisting of separate packs of
(a) an effective amount of a compound of the formula I and/or pharmaceutically usable derivatives, solvates and stereoisomers thereof and salts thereof, including mixtures thereof in all ratios, and
(b) an effective amount of a further medicament active ingredient.

The set comprises suitable containers, such as boxes or cartons, individual bottles, sachets or ampoules. The set can comprise, for example, separate ampoules each containing an effective amount of a compound of the formula I and/or pharmaceutically usable derivatives, solvates and stereoisomers thereof and salts thereof, including mixtures thereof in all ratios, and an effective amount of a further medicament active ingredient in dissolved or lyophilised form.

The invention furthermore relates to the use of the compounds of the formula I and the pharmaceutically usable prodrugs, derivatives, solvates and stereoisomers of the compounds of the formula I and the salts thereof, including mixtures thereof in all ratios, for the preparation of a medicament for combating the above-mentioned diseases in which GPIIbIIIa, $\alpha_v$ integrins, preferably $\alpha_v\beta_6$ and/or $\alpha_v\beta_3$ integrin, play a role, thus, in particular, in circulatory diseases, pathological connecting tissue proliferation in organs and fibroses, hornification disorders, tumour diseases, osteolytic diseases, pathologically angiogenic diseases, infections and for influencing wound-healing processes.

The medicaments according to the invention and the pharmaceutical compositions comprising them can be used in human or veterinary medicine. They can be administered locally or systemically, orally, intravenously, intraperitoneally, intramuscularly, subcutaneously, transdermally, nasally, buccally or iontophoretically, including formulations in suspensions, emulsions or solutions, liposomes, ointments, pastes, biodegradable polymers or as nanoparticles, tablets, capsules or pills, granules or powders, as aerosol for inhalation, as intranasal drops or sprays. Combination with other techniques, such as surgery, irradiation, diagnosis, radiotherapy, photodynamic therapy and gene therapy, and with other medicaments is also possible. Medicaments of this type may originate, for example, from the cardiovascular, central nervous system or oncology areas. They may be antitumour agents, such as angiogenesis inhibitors or cytostatics, chemotherapeutic agents from the groups of the alkylating agents, antibiotics, antimetabolites, biological agents and immunomodulators, hormones and antagonists thereof, mustard gas derivatives, alkaloids and others, where these substances may be of low molecular weight and high molecular weight. They may be lipids, carbohydrates, proteins. These include, inter alia, cytokines, toxins, fusion proteins, monoclonal antibodies and vaccines.

Suitable excipients for the pharmaceutical compositions according to the invention are organic or inorganic substances which are suitable for enteral (for example oral), parenteral, topical administration or for administration in the form of an inhalation spray and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, suitable for topical application are ointments, creams or powders. The novel compounds may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances, dyes, flavours and/or one or more further active ingredients, for example one or more vitamins.

For administration as an inhalation spray, it is possible to use sprays in which the active ingredient is either dissolved or suspended in a propellant gas or propellant-gas mixture (for example $CO_2$ or chlorofluorocarbons). The active ingredient is advantageously used here in micronised form, in which case one or more additional physiologically acceptable solvents may be present, for example ethanol. Inhalation solutions can be administered with the aid of conventional inhalers.

The substances according to the invention can generally be administered analogously to other known, commercially available peptides (for example described in U.S. Pat. No. 4,472,305), preferably in doses between about 0.05 and 500 mg, in particular between 0.5 and 100 mg, per dosage unit. The daily dose is preferably between about 0.01 and 20 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Parenteral administration is preferred.

The novel compounds of the formula I can furthermore be used in analytical biology and molecular biology.

The compounds of the formula I which contain a fluorescent dye radical can be used as diagnostic markers in the FACS (Fluorescence Activated Cell Sorter) technique and fluorescence microscopy in vitro and in vivo.

The use of labelled compounds in fluorescence microscopy is described, for example, by Y.-L. Wang and D. L. Taylor in "Fluorescence Microscopy of Living Cells in Culture, Part A+B, Academic Press, Inc. 1989". A further example of use in vivo is revealed in M. Dellian et al. Am. J. Pathol. 149, 59-71 (1996).

The compounds according to the invention can also be used as integrin ligands for the production of columns for affinity chromatography for the purification of integrins. The complex comprising an avidin-derivatised support material, for example Sepharose, and the novel compounds is formed by methods known per se (for example E. A. Bayer and M. Wilchek in Methods of Biochemical Analysis Vol 26 The Use of the Avidin-Biotin Complex as a Tool in Molecular Biology). Suitable polymeric support materials here are the polymeric solid phases, preferably having hydrophilic properties, known per se in peptide chemistry, for example crosslinked polysugars, such as cellulose, Sepharose or Sephadex$^R$, acrylamides, polymers based on polyethylene glycol or Tentakelpolymere$^R$.

EXAMPLES

Above and below, all temperatures are indicated in ° C.

The HPLC analyses (retention time Rt) were carried out in the following systems:

Column 5 μm LichroSpher 60 RP-Select B (250-4), with a 50 minute gradient from 0 to 80% of acetonitrile in water/0.1% of trifluoroacetic acid, at a flow rate of 1 ml/min and with detection at 215 nm.

Mass spectrometry (MS): EI (electron impact ionisation) M$^+$

FAB (fast atom bombardment) (M+H)$^+$

Example 1

Synthesis of Ac-Arg-Dap-Asp-Leu-Asp-Ser-Leu-Arg-NH (SEQ ID NO: 17)

a) 1 g of aminoxanthenyl resin (Novabiochem) is swollen with Fmoc-Arg(Pbf)/HOBt/DIC in 10 ml of DMF and shaken for 2 h at RT. For work-up, the solid phase was filtered off and washed 3 times with each of dichloromethane, DMF, dichloromethane and methanol and dried under reduced pressure.

b) The solid phase is suspended in DMF, and a 50% solution of piperidine in DMF is subsequently added, and the mixture is shaken for 15 min at RT. The solid phase is subsequently filtered off, and the same procedure is repeated twice. Finally, the solid phase is washed three times with each of DMF, dichloromethane and methanol and dried under reduced pressure at RT.

c) The Arg(Pbf)-NH-xanthenyl resin is subjected successively to procedure a and b for the amino acid derivatives 1. Fmoc-Leu, Fmoc-Ser(But), Fmoc-Asp(OBut), Fmoc-Leu, Fmoc-Asp(OBut), Fmoc-Dap(Boc), and 7. Fmoc-Arg (Pbf), giving Arg(Pbf)-Dap(Boc)-Asp(OBut)-Leu-Asp (OBut)-Ser(But)-Leu-Arg(Pbf)-NH-xanthenyl resin (SEQ ID NO: 18).

d) The peptidyl resin is swollen in 10 ml of DMF/pyridine/acetic anhydride (15:3:2 vol) and filtered off after 15 min at RT. For work-up, the resin is washed three times with each of DMF, dichloromethane and methanol and dried overnight under reduced pressure, giving Ac-Arg(Pbf)-Dap (Boc)-Asp(OBut)-Leu-Asp(OBut)-Ser(But)-Leu-Arg (Pbf)-NH-xanthenyl resin (SEQ ID NO: 18).

e) The side chain-protected peptidyl resin acetylated on the N terminal is mixed with 20 ml of a 98% solution of TFA in water and shaken for 3 h at RT. The solid phase is removed by filtration, and the filtrate is evaporated to dryness under reduced pressure at 37 C and freeze-dried after taking up with water, giving the desired product Ac-Arg-Dap-Asp-Leu-Asp-Ser-Leu-Arg-NH$_2$(SEQ ID NO: 17) as flocculent solid.

f) Purification of the crude product from 1e) is achieved by RP-HPLC on Lichroprep RP18 in water/0.1% of TFA with a gradient from 1-80% of 2-propanol. The desired product is obtained in high purity and has the expected mass of (M+H)+=1001 g/mol.

Example 2

Synthesis of Ac-Arg-Dap(Psa)-Asp-Leu-Asp-Ser-Leu-Arg-NH$_2$(SEQ ID NO: 2)

Fmoc was cleaved off from Asp(OBut)-Leu-Asp(OBut)-Ser(But)-Leu-Arg(Pbf)-NH-xanthenyl resin (SEQ ID NO: 19), and Fmoc-Dap(ivDde) (from Novabiochem) was coupled in a double coupling (2/1 eq.; 20/40 min). After capping and washing, the Fmoc protecting group was cleaved off using morpholine/DMF (1:1) (100 ml in 25 min), and Fmoc-Arg(Pbf) was coupled in the manner just described.

Fmoc was cleaved off normally, and capping (acetylation) and washing were carried out. The Kaiser test was negative. The ivDde protecting group was cleaved off for 10 min (10 ml/min) using 2% hydrazine in DMF: the Kaiser test was positive. Washing and drying were carried out; the yield was 2.19 g.

The partially side-protected Ac-Arg(Pbf)-Dap-Asp (OBut)-Leu-Asp(OBut)-Ser(But)-Leu-Arg(Pbf)-NH-xanthenyl resin (SEQ ID NO: 20) was divided into 16 aliquots of 130 mg, which were swollen briefly in DCM.

The corresponding sulfonyl chloride was dissolved in 1.5 ml of DCM in the Eppendorf vessel, and 5 eq. of DIEA were added. The solutions were added to the resin. When the Kaiser test was still slightly positive after 1 h, the resin was filtered off, washed and re-coupled in the same way. It was washed thoroughly with DMF, DCM and isopropanol and dried.

Cleaving off for 2 hours with in each case 6 ml of TFA/water/TIS (94/3/3) filtration and purification by RP-HPLC gives the free peptide derivatives; for example the product Ac-Arg-Dap(Psa)-Asp-Leu-Asp-Ser-Leu-Arg-NH$_2$ (SEQ ID NO: 2) on use of phenylsulfonyl chloride.

Example 3

Analogously to Example 2, the following products, inter alia, were prepared in that the amino acid X in position 2 of the peptide Ac-Arg-X-Asp-Leu-Asp-Ser-Leu-Arg-NH2 (SEQ ID NO: 21) was obtained through the use of the corresponding Fmoc-amino acid derivatives instead of Fmoc-Dap (ivDde) and the corresponding acylating reagents instead of phenylsulfonyl chloride. They can also be prepared through the use of the ready-prepared amino acid derivatives, such as Fmoc-Dap(SO$_2$Ph)-OH (and the analogues) in the peptide synthesis.

| Sequence | SEQ ID NO: | Rt[min] HPLC | Empirical formula | M + H+ g/mol calc. | M + H+ g/mol found |
|---|---|---|---|---|---|
| Ac-R-Dap(Psa)-DLDSLR-NH2 | 2 | 15.78$^D$ | $C_{46}H_{76}N_{16}O_{16}S$ | 1141.5423 | 571(2H+) |
| Ac-R-Dap(F5-Psa)-DLDSLR-NH2 | 3 | 18.14$^D$ | $C_{46}H_{71}F_5N_{16}O_{16}S$ | 1231.4951 | 616(2H+) |
| Ac-R-Dap(2-NO2-Psa)-DLDSLR-NH2 | 4 | 15.90$^D$ | $C_{46}H_{75}N_{17}O_{18}S$ | 1186.5273 | 594(2H+) |
| Ac-R-Dap(4-NO2-Psa)-DLDSLR-NH2 | 5 | 16.50$^D$ | $C_{46}H_{75}N_{17}O_{18}S$ | 1186.5273 | 594(2H+) |
| Ac-R-Dap(2,4-NO2-Psa)-DLDSLR-NH2 | 6 | 17.53$^D$ | $C_{46}H_{74}N_{18}O_{20}S$ | 1231.5124 | 616(2H+) |
| Ac-R-Dap(6-OMe-Psa)-DLDSLR-NH2 | 7 | 15.49$^D$ | $C_{47}H_{78}N_{16}O_{17}S$ | 1171.5528 | 586(2H+) |

-continued

| Sequence | SEQ ID NO: | Rt[min] HPLC | Empirical formula | M + H+ g/mol calc. | M + H+ g/mol found |
|---|---|---|---|---|---|
| Ac-R-Dap(2-CF3-Psa)-DLDSLR-NH2 | 8 | 16.86$^D$ | $C_{47}H_{75}F_3N_{16}O_{16}S$ | 1209.5297 | 605(2H+) |
| Ac-R-Dap(3-CF3-Psa)-DLDSLR-NH2 | 9 | 16.00$^D$ | $C_{47}H_{75}F_3N_{16}O_{16}S$ | 1209.5297 | 605(2H+) |
| Ac-R-Dap(Me5-Psa)-DLDSLR-NH2 | 10 | 19.60$^D$ | $C_{51}H_{86}N_{16}O_{16}S$ | 1211.6205 | 606(2H+) |
| Ac-R-Dap(4-tBu-Psa)-DLDSLR-NH2 | 11 | 19.87$^D$ | $C_{50}H_{84}N_{16}O_{16}S$ | 1197.6049 | 599(2H+) |
| Ac-R-Dap(Bsa)-DLDSLR-NH2 | 12 | 15.61$^D$ | $C_{47}H_{78}N_{16}O_{16}S$ | 1155.5579 | |
| Ac-R-Dap(iPrs)-DLDSLR-NH2 | 13 | 10.97$^D$ | $C_{43}H_{78}N_{16}O_{16}S$ | 1107.5579 | 554(2H+) |
| Ac-R-Dap(1-Nap)-DLDSLR-NH2 | 14 | 17.60$^D$ | $C_{50}H_{78}N_{16}O_{16}S$ | 1191.5579 | 596(2H+) |
| Ac-R-Dap(2-Nap)-DLDSLR-NH2 | 15 | 17.99$^D$ | $C_{50}H_{78}N_{16}O_{16}S$ | 1191.5579 | 596(2H+) |
| Ac-R-Dap(4-Ph-Psa)-DLDSLR-NH2 | 16 | 19.65$^D$ | $C_{52}H_{80}N_{16}O_{16}S$ | 1217.5736 | 609(2H+) |

Nomenclature for amino acids in accordance with Eur. J. Biochem. 138, 9-37 (1984)
$^D$HPLC system: solvent: A = 0.1% of TFA; B = 80% of acetonitrile/0.1% of TFA; gradient: 1% of B to 99% of B in 50 min; column: Merck, LiChrosphere 60 250-4, RP-select B: 5 µm; flow rate: 1 ml/min; detection: 215 nm.

Example 4

Influence of Soluble Substances on the Binding of Biotinylated Fibronectin to $\alpha_v\beta_6$ The prepared peptides according to the invention together with competing fibronectin were bound in solution to the immobilised $\alpha_v\beta_6$ receptor, and the Q value as a measure of the selectivity of the binding of the peptide to be tested to $\alpha_v\beta_6$ was determined. The Q value is calculated from the quotient of the $IC_{50}$ values of test peptide and a standard. The standard used was the linear Ac-RTDLDSLR-NH$_2$(SEQ ID NO: 22) (WO01/00660; Pytela et al., 1986, Science 231, 1559). The binding test was carried out in detail as follows:

$\alpha_v\beta_6$ was immobilised on microtitre plates by dilution of the protein solution in TBS++ and subsequent incubation overnight at 4° C. (100 µl/well). Non-specific binding sites were blocked by incubation (2 h; 37° C.) with 3% (w/v) BSA in TBS++ (200 µl/well). Excess BSA was removed by washing three times with TBSA++. Peptides were diluted serially (1:10) in TBSA++ and incubated together with biotinylated fibronectin (2 µg/ml) with the immobilised integrin (50 µl of peptide+50 µl of ligand per well, 2 h; 37° C.).

Unbound fibronectin and peptides were removed by washing three times with TBSA++. The bound fibronectin was detected by incubation (1 h; 37° C.) with an alkaline phosphatase-coupled antibiotin antibody (1:20000 in TBSA++; 100 µl/well). After washing three times with TBSA++, the colorimetric detection was carried out by incubation (10-15 min; 25° C.; in the dark) with substrate solution (5 mg of nitrophenyl phosphate, 1 ml of ethanolamine, 4 ml of H$_2$O (100 µl/well)). The enzyme reaction was stopped by addition of 0.4M NaOH (100 µl/well). The colour intensity was determined at 405 nm in the ELISA measuring instrument and adjusted against a blank value. The blank value used was wells which were not coated with receptor. The standard employed in each experiment was Ac-RTDLDSLR-NH2 (SEQ ID NO: 22), which has an $IC_{50}$ value<100 nM.

$IC_{50}$ values for the peptides tested were read off from a graph, and the Q value of the peptide was determined therefrom together with the $IC_{50}$ of the standard.

It was found in these experiments that a large number of the compounds synthesised have submicromolar to nanomolar affinity to integrin $\alpha_v\beta_6$ (see Table 1).

TABLE 1

| Sequence | SEQ ID NO: | Q |
|---|---|---|
| Ac-R-Dap(Psa)-DLDSLR-NH2 | 2 | 0.20 |
| Ac-R-Dap(F5-Psa)-DLDSLR-NH2 | 3 | 3.7 |
| Ac-R-Dap(2-NO2-Psa)-DLDSLR-NH2 | 4 | 0.27 |
| Ac-R-Dap(4-NO2-Psa)-DLDSLR-NH2 | 5 | 1.5 |
| Ac-R-Dap(2,4-NO2-Psa)-DLDSLR-NH2 | 6 | 1.5 |
| Ac-R-Dap(6-OMe-Psa)-DLDSLR-NH2 | 7 | 1.4 |
| Ac-R-Dap(2-CF3-Psa)-DLDSLR-NH2 | 8 | 0.29 |
| Ac-R-Dap(3-CF3-Psa)-DLDSLR-NH2 | 9 | 0.97 |
| Ac-R-Dap(Me5-Psa)-DLDSLR-NH2 | 10 | 0.97 |
| Ac-R-Dap(4-tBu-Psa)-DLDSLR-NH2 | 11 | 69 |
| Ac-R-Dap(Bsa)-DLDSLR-NH2 | 12 | 4.1 |
| Ac-R-Dap(iPrs)-DLDSLR-NH2 | 13 | 57 |
| Ac-R-Dap(1-Nap)-DLDSLR-NH2 | 14 | 0.71 |
| Ac-R-Dap(2-Nap)-DLDSLR-NH2 | 15 | 5.1 |
| Ac-R-Dap(4-Ph-Psa)-DLDSLR-NH2 | 16 | 4.8 |
| AC-RTDLDSLR-NH2 | 21 | 1.00 |

Q value = $IC_{50}$ test peptide/$IC_{50}$ standard
Q values from experiment repetitions were averaged The examples below relate to pharmaceutical compositions:

Example A

Injection Vials

A solution of 100 g of the compound of the formula I according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of compound of the formula I according to the invention is melted with 100 g of soya lecithin and 1400 g of cocoa butter, poured into moulds and allowed to cool. Each suppository contains 20 mg of active ingredient.

Example C

Solution

A solution is prepared from 1 g of compound of the formula I according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water The pH is adjusted to 6.8, and the solution is made up to 1 l and sterilised by irradiation. This solution can be used in the form of eye drops.

Example D

Ointment 500 mg of compound of the formula I according to the invention are mixed with 99.5 g of Vaseline under aseptic conditions.

Example E

Tablets

A mixture of 1 kg of compound of the formula I according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, tragacanth and dye.

Example G

Capsules 2 kg of compound of the formula I according to the invention are introduced into hard gelatine capsules in a conventional manner in such a way that each capsule contains 20 mg of the active ingredient.

Example H

Ampoules

A solution of 1 kg of compound of the formula I according to the invention in 60 l of bidistilled water is sterile filtered, transferred into ampoules, lyophilised under sterile conditions and sealed under sterile conditions. Each ampoule contains 10 mg of active ingredient.

Example I

Inhalation Spray 14 g of compound of the formula I according to the invention are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

---

We claim:

1. A peptide compound of formula I $$R^1\text{-Arg-X-Asp-Leu-Asp-Ser-Leu-Arg-}R^2 \text{ (SEQ ID NO: 1)} \quad \text{I}$$

wherein
$R^1$ is H, acetyl or acyl and
$R^2$ is —OH, $OR^3NH_2$, $NHR^3$, $N(R^3)_2$
$R^3$ is alkyl, aralkyl, aryl, Het and
X is an amino acid of formula II

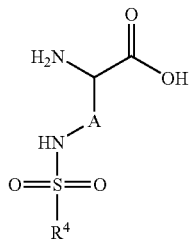

wherein
A is $(CH_2)_n$
$R^4$ is H, alkyl, aralkyl or aryl, and
n is 1, 2, 3, 4, 5 or 6,
and wherein the amino acid of formula II is bonded to the adjacent Arg via a peptide bond of the α-amino group and to the α-amino group of the adjacent Asp via a peptide bond of the α-carboxyl group,
or a pharmaceutically acceptable stereoisomer thereof or a salt thereof.

2. The peptide compound according to claim 1 which is
Ac-Arg-Dap (Psa)-Asp-Leu-Asp-Ser-Leu-Arg-NH₂, (SEQ ID NO: 2)
Ac-Arg-Dap (F5-PSA)-Asp-Leu-Asp-Ser-Leu-Arg-NH₂, (SEQ ID NO: 3)
Ac-Arg-Dap (2-NO₂—PSA)-Asp-Leu-Asp-Ser-Leu-Arg-NH₂, (SEQ ID NO: 4)
Ac-Arg-Dap(4-NO₂—PSA)-Asp-Leu-Asp-Ser-Leu-Arg-NH₂, (SEQ ID NO: 5)
Ac-Arg-Dap(2,4-NO₂—PSA)-Asp-Leu-Asp-Ser-Leu-Arg-NH₂, (SEQ ID NO: 6)
Ac-Arg-Dap (6-OMe-PSA)-Asp-Leu-Asp-Ser-Leu-Arg-NH₂, (SEQ ID NO: 7)
Ac-Arg-Dap(2-CF₃—PSA)-Asp-Leu-Asp-Ser-Leu-Arg-NH₂, (SEQ ID NO: 8)
Ac-Arg-Dap(3-CF₃—PSA)-Asp-Leu-Asp-Ser-Leu-Arg-NH₂, (SEQ ID NO: 9)
Ac-Arg-Dap(Me₅-PSA)-Asp-Leu-Asp-Ser-Leu-Arg-NH₂, (SEQ ID NO: 10)
Ac-Arg-Dap(4-tBu-PSA)-Asp-Leu-Asp-Ser-Leu-Arg-NH₂, (SEQ ID NO: 11)
Ac-Arg-Dap(BSA)-Asp-Leu-Asp-Ser-Leu-Arg-NH₂, (SEQ ID NO: 12)
Ac-Arg-Dap(iPrs)-Asp-Leu-Asp-Ser-Leu-Arg-NH₂, (SEQ ID NO: 13)
Ac-Arg-Dap(1-Nap)-Asp-Leu-Asp-Ser-Leu-Arg-NH₂, (SEQ ID NO: 14)
Ac-Arg-Dap(2-Nap)-Asp-Leu-Asp-Ser-Leu-Arg-NH₂, or (SEQ ID NO: 15)
Ac-Arg-Dap(4-Ph-Psa)-Asp-Leu-Asp-Ser-Leu-Arg-NH₂, (SEQ ID NO: 16)
or a pharmaceutically acceptable stereoisomer thereof or a salt thereof.

3. A pharmaceutical composition comprising a peptide compound of the formula I according to claim 1 and an acceptable carrier.

4. A medicament comprising an effective amount of a peptide compound of the formula I according to claim 1 and at least one inert excipient, adjuvant, diluent or a combination thereof.

5. The pharmaceutical preparation according to claim 3, further comprising a detectable moiety.

6. A process for preparing a pharmaceutical composition comprising combining the peptide compound of the formula I according to claim 1 with one or more inert excipients and/or diluents.

7. A method for treating a disease mediated by blood platelet integrin GPIIbIIIa and/or $α_v$ integrins comprising administering to a subject in need thereof the peptide compound of the formula I according to claim 1.

8. A kit comprising in one or separate packages
(a) an effective amount of the peptide compound of the formula I according to claim 1 and
(b) a carrier or an excipient.

9. A method according to claim 7 wherein the integrin is $α_vβ_6$ and/or $α_vβ_6$ integrin.

* * * * *